(12) United States Patent
Huang et al.

(10) Patent No.: US 6,365,787 B1
(45) Date of Patent: Apr. 2, 2002

(54) COMPOUNDS FOR THE SUPPRESSION OF HIV TAT TRANSACTIVATION

(75) Inventors: Ru Chih C. Huang; John N. Gnabre, both of Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 08/316,341

(22) Filed: Sep. 30, 1994

(51) Int. Cl.⁷ .............................................. C07C 39/12
(52) U.S. Cl. ........................ 568/729; 514/885; 514/934
(58) Field of Search .......................... 568/729; 514/934, 514/885

(56) References Cited

PUBLICATIONS

Huang et al., Regulation of HIV Promoter Activities in Human Embryonal Carcinoma Cells, NTERA–2, Aids And Human Retroviruses—Gene Regulation and Aids, pp. 147–160.
Giza et al., "A Self–Inducing Runaway–Replication Plasmid Expression System Utilizing the Rop Protein", Gene 78 (1989), pp 73–84.
Staal et al., "Antioxidants Inhibit Stimulation of HIV Transcription", AIDS Research and Human Retroviruses, vol. 9, No. 4, 1993, pp 299–306.
Weislow et al., "New Soluble–Formazan Assay for HIV–1 Cytopathic Effects: Application to High–Flux Screening of Synthetic and Natural Products for AIDS–Antiviral Activity", Journal of the National Cancer Institute, vol. 81, No. 8, Apr. 19, 1989, pp 577–586.
Gisvold et al. "Lignans from *Larrea divaricata*"; vol. 63, No. 12, Dec. 1974; pp. 1905–1907.
C. W. Perry, et al., J. Org Chem., vol. 37, No. 26, 1972, pp. 4371–4376.*

* cited by examiner

Primary Examiner—John W. Rollins
(74) Attorney, Agent, or Firm—Cushman Darby & Cushman, LLP

(57) ABSTRACT

The present invention reveals the isolation, purification and characterization from the creosote bush Larrea tridentata of compounds of the structural formula:

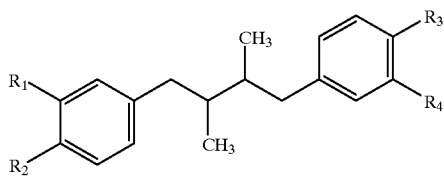

where $R_1$, $R_2$, $R_3$ and $R_4$ are each selected from the group consisting of HO—, $CH_3O$— and $CH_3(C=O)O$—, provided that $R_1$, $R_2$, $R_3$ and $R_4$ are not each HO—0 simultaneously. Each compound is a derivative of 1,4-bis-(3,4-dihydroxyphenyl)-2,3-dimethylbutane (nordihydroquaiaretic acid, NDGA). In addition, NDGA and each derivative can be used in a method to suppress Tat transactivation of a lentivirus, including the HIV virus, in a cell by administering NDGA or a derivative of NDGA to the cell.

8 Claims, 7 Drawing Sheets

COMPOUNDS FOR THE SUPPRESSION OF HIV TAT TRANSACTIVATION

The invention described and claimed herein was made in part with funds from Grant No. AI 32301 from the National Institutes of Health and in part with funds from U.S Army Medical Research Grant DAMD 17-93C3122. The U.S. Government has certain rights in the invention.

BACKGROUND OF THE INVENTION

1. Field of the Invention

The present invention relates to the isolation, purification and characterization of derivatives of 1,4-bis-(3,4-dihydroxyphenyl)-2,3-dimethylbutane (nordihydroquaiaretic acid, NDGA). The derivatives were isolated from leaf and flower extracts of the creosote bush (*Larrea tridentata*, Zygophyllaceae) and together with NDGA can be used to suppress Tat transactivation in lentiviruses, including the HIV virus.

2. Description of the Related Art

Tat is a transactivator of human immunodeficiency virus (HIV) gene expression and is one of the two or more necessary viral regulatory factors (Tat and Rev) for HIV gene expression. Tat acts by binding to the TAR RNA element and activating transcription from the long terminal repeat (LTR) promoter.

The Tat protein stabilizes elongation of transcription and has also been shown to be involved in transcription initiation. Previous studies have shown that Tat mediates reduction of antibody-dependent T cell proliferation, contributing substantially to the failure of the immune response. Tat also directly stimulates Kaposi's cell growth.

Since Tat has no apparent cellular homologs, this strong positive regulator has become an attractive target for the development of anti-AIDS drugs (see FIG. 1). In contrast to currently available HIV reverse transcriptase inhibitors (AZT, DDI) or potential protease inhibitors that prevent new rounds of infection, an inhibitor which suppresses viral gene Tat regulated expression of integrated proviral DNA will arrest the virus at an early stage (Hsu et al., *Science* 254:1799–1802, 1991).

Efforts aimed at the elucidation of factors which control gene expression at transcriptional and post-transcriptional levels in host eukaryotes have recently made possible quantitative assessment of Tat function (Sim, *Ann. N.Y. Acad. Sci.* 616: 64–70, 1990, the entire contents of which are hereby incorporated by reference and relied upon). To screen for inhibitors for Tat regulated transactivation (Tat-TRS), the secreted placental alkaline phosphatase (SEAP) reporter gene is put under the control of HIV-1 LTR promoter in the plasmid pBC12/HIV/SEAP. The Tat-coded activity is supplied by a second plasmid construct pBC12/CMV/t2. Transient cotransfection of COS cells with these two plasmids leads to secretion of alkaline phosphatase into the culture medium which is analyzed by a simple calorimetric assay (Berger et al., *Gene* 66: 1–10, 1988, the entire contents of which are hereby incorporated by reference and relied upon). The SEAP assay, therefore, provides an indirect determination of Tat transactivation. An inhibitor should cause reduction of the SEAP activity which is due to inhibition of the expression of the SEAP mRNA via transactivation of the HIV-1 LTR promoter by Tat protein (Tat-TRS).

SUMMARY OF THE INVENTION

In the present application, we disclose Tat-TRS inhibitory activity of the desert plant *Larrea tridentata*. Among several plant extracts prepared from rain forest and desert medicinal plants used in traditional medicinal against viral affections, only the total extract from the leaves and flowers of the creosote bush (*Larrea tridentata*) showed Tat-TRS inhibitory activity. This extract also inhibits HIV cytopathic effects on human lymphoblastoid cells chronically infected with the virus as assessed by the newly developed soluble-formazan assay (Weislow et al., *JNCI* 81: 577–586, 1989, the entire contents of which are hereby incorporated by reference and relied upon).

The present invention discloses compounds of the structural formula:

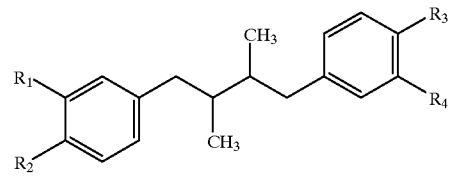

wherein $R_1$, $R_2$, $R_3$ and $R_4$ are each selected from the group consisting of HO—, $CH_3O$— and $CH_3(C=O)O$—, provided that $R_1$, $R_2$, $R_3$ and $R_4$ are not each HO— simultaneously.

Each compound was isolated from leaf-flower extracts of the creosote bush Larrea tridentata and is a derivative of 1,4-bis-(3,4-dihydroxyphenyl)-2,3-dimethylbutane (nordihydroquaiaretic acid, NDGA).

In addition, NDGA and each derivative can be used to suppress Pat transactivation of a lentivirus, including the HIV virus, in a cell by administering NDGA or a derivative thereof to the cell.

DETAILED DESCRIPTION OF THE PREFERRED EMBODIMENTS

Figure 1:
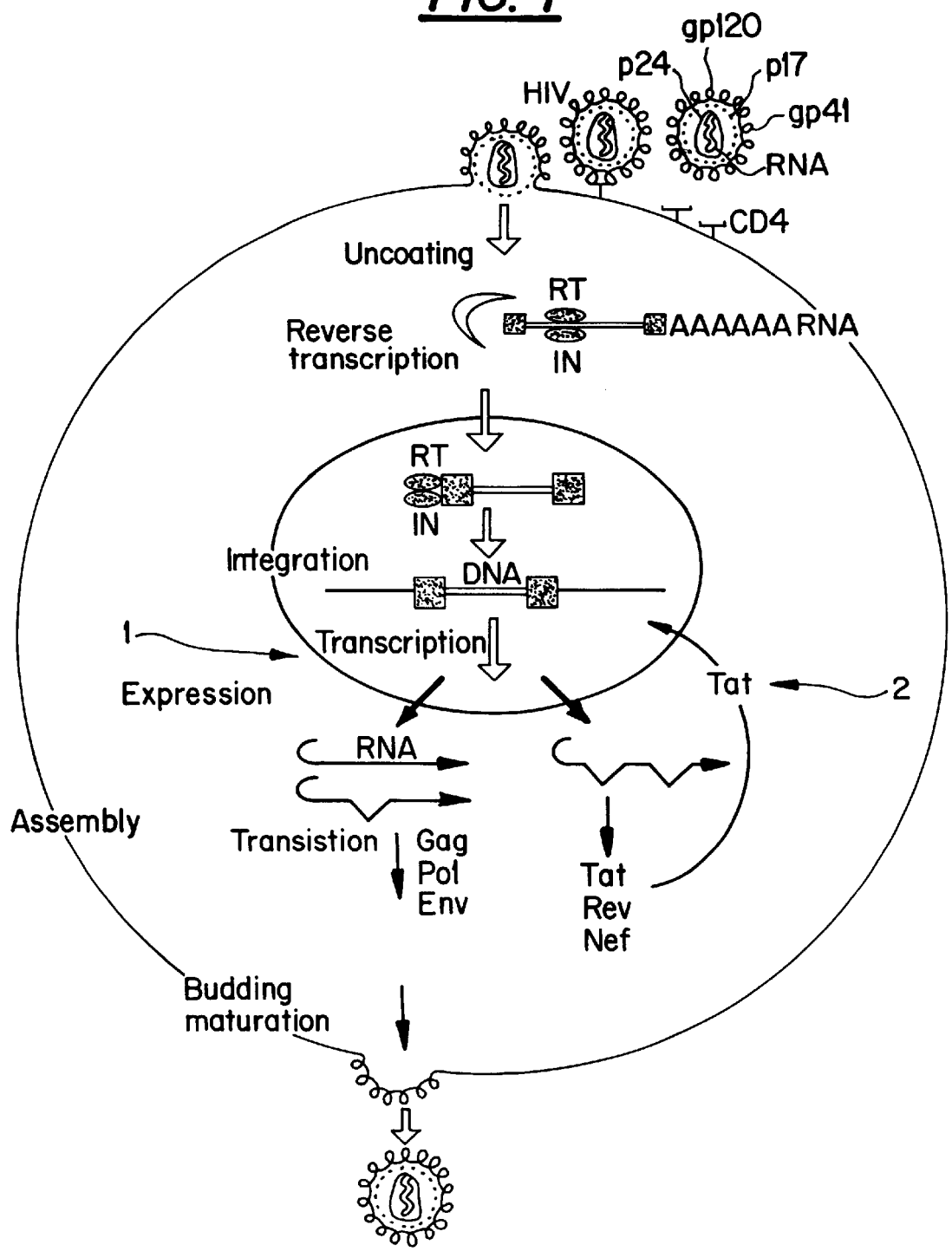
FIG. 1 graphically illustrates the life cycle of HIV-1 and different sites of action of potential therapeutic agents including Tat-TRS inhibitors. The basal transcription step is indicated by 1 and the viral regulatory protein dependent transactivation step by 2.

The present invention discloses the isolation, purification and characterization of derivatives of 1,4-bis-(3,4-dihydroxyphenyl)-2,3-dimethylbutane or nordihydroquaiaretic acid (NDGA). Each derivative of NDGA was isolated, purified and characterized according to the following procedures.

Materials and Methods

Cell line: COS-7 cells with SV40 origin of replication were maintained in Isocove's Modified Dulbecco's Medium (IMDM) supplemented with 10% fetal calf serum (FCS) and antibiotics. Cells were incubated in a humidified 95% $O_2$/5% $CO_2$ incubator at 37° C.

Plasmids: The plasmid pBC12/HIV/SEAP containing the Tat-sensitive HIV LTR promoter with the SEAP reporter gene but no Tat-coded function was used to express SEAP basal activity; pBC12/CMV/t2 supplied the Tat-coded function, i.e., the induced SEAP level. pBC12/RSV/SEAP containing the constitutive Tat-insensitive LTR promoter of Rous Sarcoma Virus (RSV) served as a positive control. All plasmids were obtained from Dr. Bryan Cullen, Duke Medical Center. PlasmidE pSEAP and pBKCMV and HIV LTR and Tat DNA are commercially available from Clontech and Stratagene. Plasmid transformation was achieved in E. coli MC1061 strain, which was obtained from Dr. Barbara Bachmann, Department of Biology Yale University. E. coli MC1061 strain can also be purchased from Clontech. Plasmid DNAs were purified using Qiagen® purification kit (Qiagen).

Chemical Reagents: Diethanolamine (#31589) and p-nitrophenylphosphate (#71768) were purchased from Fluka BioChemika, and L-homoarginine (#H-1007) was purchased from Sigma Co. The lipospermine DOGS (Transfectam®, #E123 A, Promega) was used in DNA transfection studies.

Preparation of Plant Testing Materials: The leaves and flowers of the creosote bush were collected based on ethnopharmacological inquiries. Plant materials were dried and ground in a 3 mm screen Willy mill. In pilot studies, 1 g of the plant powder was initially extracted by successive macerations using a mixture of chloroform:methanol. The extract was concentrated to residue. The entire 176 mg of the crude extract generated were treated 7 times with 3 ml of hexane. This step afforded 137 mg of hexane-insoluble (HI) materials and 31 mg of hexane-soluble (HS) materials. All these extracts were monitored stepwise by $SiO_2$ TLC with cerium sulfate charring, 2% $CeSO_4$ (w/V) in 5.6% $H_2SO_4$ (v/v), and by the SEAP assay for anti Tat-TRS activity.

For the SEAP assay, test materials were dissolved in 10% DMSO solution made in calcium/magnesium-free PBS. The suspension was centrifuged and the stock solution (10 mg/ml) was filter-sterilized using a Millex®-GS 22 μm filter (Millipore). Appropriate dilutions of the stock solution were prepared in a final DMSO concentration of 0.2% in PBS to obtain the various concentrations of test compounds.

Differential Fractionation and Purification of the Active Ingredient by Countercurrent Chromatography (CCC): Based on the preliminary results of the above fractions in the SEAP assay, further fractionation of the active HI fraction by CCC was undertaken. This led to the identification of two major active fractions denoted "Green" and "Yellow" components. Identification of the most active fractions from these prospective studies prompted a full scale differential fractionation of plant powder in the attempt to generate a large quantity of the Green and Yellow fractions. This fractionation was carried out on 101.4 g of plant powder, and started with a hexane treatment step, as outlined in Table 1.

Further fractionation of the major components from the organic phase (OG) obtained after chloroform:water partition was achieved by countercurrent liquid-liquid partition chromatography using the versatile cross-axis planet centrifuge (CPC) as described by Ito and Conway, *CRC Critical Reviews of Analytical Chemistry* 17: 65 et seq., 1986, the entire contents of which are hereby incorporated by referenced and relied upon. The optimal solvent system was a mixture of hexane:EtOAC:MeOH:0.5% NaCl in the ratio of 6:4:5:5, with the upper phase (organic layer) as the mobile phase. Five g of the organic fraction were dissolved in 23 ml of a mixture of the two phases and introduced into the coil via a loop valve. The mobile phase pumped through the coil while rotating it at 800 rpm. At a flow rate of approximately 4 ml per minute, approximately 32% of the stationary phase was initially lost (68% retention). After the appearance of mobile phase in the elute, fractions of mobile phase were collected, evaporated to dryness, monitored by TLC and pooled accordingly into 5 batches: Solvent front (SF), Green (Gr), Yellow (Ye), Red and Stationary phase (StP). All these fractions were then monitored by the SEAP assay for anti Tat-TRS activity.

Further purification of the Green and Yellow fractions was achieved by CCC using an epicyclic coil planet centrifuge known as the Ito multilayer coil separator-extractor (Ito and Conway, *CRC Critical Reviews of Analytical Chemistry* 17: 65 et seq., 1986, the entire contents of which are hereby incorporated by reference and relied upon). The solvent system was a mixture of hexane:EtOAC:MeOH:0.5% NaCl (7:3:5:5). Two hundreds mg of Green fraction afforded 6.8 mg of a component termed Gr, i.e., ≈0.051% total yield based on the original plant powder. Similar studies on the Yellow fraction (Ye) generated 9.3 mg of a component denoted Lo. These purified components (Lo and Gr) each consists of several compounds, and their respective "mother" fractions were stored at 4° C. until tested for biological activity and used for further characterization.

TABLE 1

DIFFERENTIAL FRACTIONATION AND COUNTERCURRENT CHROMATOGRAPHY (CCC) OF NDGA DERIVATIVES FROM THE CREOSOTE BUSH, *LARREA TRIDENTATA*.

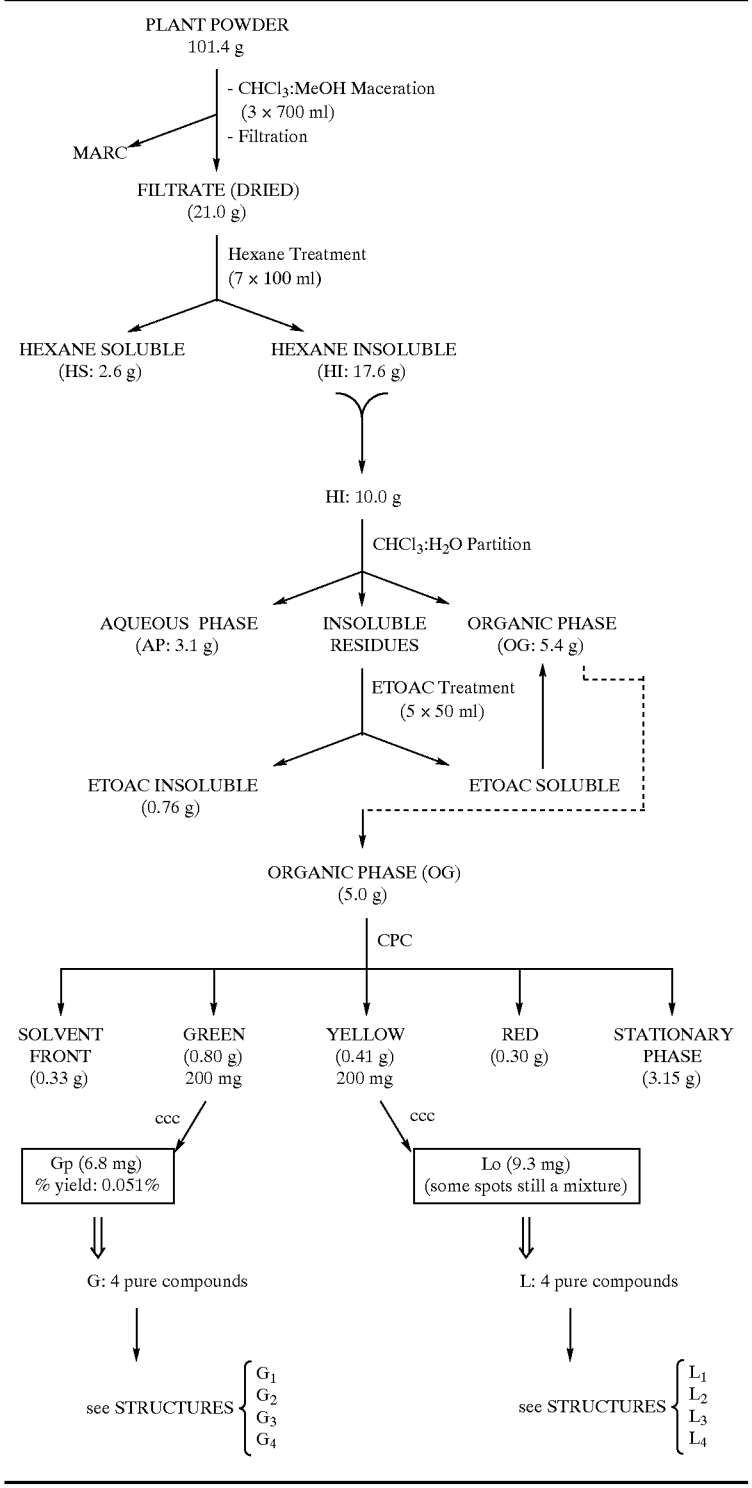

Cell Culture and DNA Transfection: COS cells were maintained as previously described (Cullen, *Cell* 46: 973–982, 1986, the entire contents of which are hereby incorporated by reference and relied upon). DNA transfection was performed using a modified procedure of the lipospermine (Transfectam®, Promega #E123A) method originally described elsewhere (Loeffler and Behr, *Methods in Enzymology* 217: 599–618, 1993, the entire contents of which are hereby incorporated by reference and relied upon). Briefly, a day before DNA transfection, Linbro® 24 flat bottom well of 17-mm diameter plates were pretreated with 0.5 ml sterile solution of 0.1% gelatin. The plates were kept in the hood for 1 hour (all transfection steps were performed in the hood, unless otherwise stated). The gelatin solution was aspirated and the plates were washed with 0.5 ml of IMDM supplemented with 10% fetal calf serum and antibiotics (complete medium). COS cells were seeded at a density of ≈$1.5 \times 10^5$ cells per 17-mm plate and incubated in a humidified 95% $O_2$/5% $CO_2$ incubator at 37° C. DNA transfection was performed at 30–50% cell confluency. The stock solution of the Transfectam reagent, DOGS, was prepared according to the manufacturer's advice at 1 mg/0.380 ml (2.38 mg/ml or 3.4 mM) in 10% (v/v) ethanol in distilled water.

The transfection cocktail consisted of two solutions prepared in sterile tubes:

a) Solution A contained a sterile 150 mM NaCl solution+ plasmid DNAs (non selected/selected gene in 2:1 ratio): 0.35 μg of pBC12/HIV/SEAP per well+0.175 μg of pBC12/CMB/t2 (coding for Tat function) per well.

b) Solution B contained an equal volume of 150 mM NaCl and a volume of Transfectam® determined to be 6 times the total amount of DNAS. Solutions A and B were homogenized and immediately mixed.

Ten minutes were allowed for the reaction to proceed. Meanwhile, the growth medium was removed from the subconfluent COS cells and 300 μl (100 μl of complete IMDM+200 μl serum-free medium) were added to each well. The transfection cocktail was dispensed to the wells in equal volume. Control samples containing no DNA were similarly treated and received sterile 150 mM NaCl solution alone. All samples were incubated for 10 to 12 hours after which 700 μl of complete growth medium were added. Test compounds prepared in 5% DMSO/Ca-Mg-free PBS (for non-water-soluble materials) were immediately added at various concentrations to the wells. Drug-untreated control samples received 5% DMSO/PBS solution alone (final DMSO concentration of 0.2%). All samples were then incubated for an additional 48 hours after which 300 μl of each culture supernatant was removed for SEAP analysis.

The Secreted Alkaline Phosphatase (SEAP) Assay: The secreted alkaline phosphatase analysis was performed as originally described (Berger et al., *Gene* 66: 1–10, 1988, the entire contents of which are hereby incorporated by reference and relied upon). Briefly, a 250-μl aliquot was removed from COS cell culture supernatants, heated at 65° C. for 5 minutes to selectively inactivate endogenous phosphatase (SEAP is heat stable) and centrifuged in a microfuge for 2 minutes. One hundred μl of 2×SEAP assay buffer (1.0 M diethanolamine, pH 9.8; 0.5 mM $MgCl_2$; 10 mM L-homoarginine) were added to 100-μl aliquot of the samples. The solution was mixed and transferred into a 96-well flat-bottom culture dish (Corning). Twenty μl of pre-warmed substrate solution (120 mM p-nitrophenylphosphate dissolved in 1×SEAP assay buffer) were dispensed with a multipipeter into each well containing the reaction mixture. $A_{405}$ of the reaction was read at 5-minute intervals at 37° C. for 60 minutes using an EL340i microplate reader (Bio-tek Instruments, Inc.) with 5-second automatic shakings before each reading. The change in absorbance was plotted against time in the standard assay of SEAP induction. In the drug screening assay, the percent inhibition of SEAP expression was calculated at 30 minutes as follows:

$$\% \text{ Inhibition} = 100 - [(CT^+ - C^+) \times 100]$$

where:

| | |
|---|---|
| $C^-$ | Control sample (no DNA, no drug) |
| $CT^-$ | Control sample (+DNA, no drug) |
| $C^+$ | Drug-treated sample (no DNA, + drug) |
| $CT^+$ | Drug-treated sample (+DNA, + drug) |

Optimization of the Transfection Technique: Various techniques are utilized in the DNA transfection of eukaryotic cells. These procedures include DNA coprecipitation with calcium phosphate or cationic polymers, cell membrane weakening either by chemical means (detergents, solvents, enzymes, amphophilic polymers) or by physical means (thermic, osmotic or electric shocks, or particle bombardment). These techniques suffer, to some extent, variable efficiency and varying degrees of cytotoxicity.

Prerequisites for cells to be amenable to DNA uptake, i.e., to cross the intact cytoplasmic membrane, are "compaction and masking of DNA charges" (Loeffler and Behr, *Methods in Enzymology* 217: 599–618, 1993). These requirements have been successfully met with the newly developed Transfectam® procedure. The Transfectam reagent (dioctadecylamidoglycyl spermine) is a synthetic cationic lipopolyamine which contains a positively charged spermine headgroup with a strong affinity for DNA ($K_d = 10^{-5} - 10^{-7}$ M). This spermine headgroup is covalently attached to a lipid moiety by a peptide bond. The lipospermine molecules bind to DNA, coating it with a lipid layer. In the presence of excess lipospermine, cationic lipid-coated plasmid DNA vesicles are formed and the lipid portion of the complex fuses with cell membrane. DNA internalization is believed to occur by endocytosis.

Transfectam-mediated transfection has been shown to offer greater efficiency than existing methods (Barthel et al., *DNA and Cell Biology* 12(6): 553–560, 1993). In addition, Transfectam® is a stable and virtually non-cytotoxic reagent. However, factors for optimization of transfection in the specific COS cell line had to be addressed. These factors include the duration of transfection, the ratio of the Transfectam reagent to DNA, DNA concentration and other dilution factors such as NaCl volume and strength. The results of optimization of transfection conditions are shown below.

a) Duration of transfection: COS cells were incubated with a fixed plasmid DNA concentration in time course studies. These studies aimed at the selection of the suboptimal incubation time point for inhibition studies of SEAP expression by various test compounds. The results of the time-course induction of SEAP expression (results not shown) indicate a gradual time-dependent increase in SEAP expression. The onset of this induction began at less than 4 hours and reached a maximum at 24 hours. No significant difference was observed between the 10, 12 and 15-hour values. Therefore, the 12–15 hours endpoint was selected as the appropriate suboptimal incubation period for inhibition of SEAP expression in all subsequent drug screen studies.

b) DNA concentration: The optimal DNA concentration for transfection was determined based on previous studies with Transfectam reagent (Loeffler and Behr, *Methods in Enzymology* 217: 599–618, 1993). For cotransfection, the ratio 2:1 (nonselected gene/selected gene) was found to be the most appropriate as reported elsewhere (Hsu et al., *Science* 254: 1799–1802, 1991, the entire contents of which are hereby incorporated by reference and relied upon). The nonselected pBC12/HIV/SEAP plasmid was utilized at a concentration of 0.35 µg/well and pBC12/CMV/t2 plasmic coding for Tat function at a concentration of 0.75 µg/well in Linbro® 24 flat bottom well of 17-mm diameter plates.

c) Ratio of Transfectam to DNA and Determination of Ionic Strength: The optimal ratio of Transfectam® (DOGS) to plasmid DNA and the ionic strength of NaCl used were a modification of the previously reported values (Loeffler and Behr, *Methods in Enzymology* 217: 1799–1802, 1993) and determined as follows: From the original 1 mg/0.400 ml (2.38 mg/ml) stock solution of Transfectam® prepared in 10% (v/v) ethanol in distilled water, 6 times the volume (µl) of stock solution was required for each µg DNA used. The optimal ionic strength of the solution was provided by an appropriate volume of 150 mM NaCl determined by the relation:

Volume (µl) of NaCl=Volume (µl) Transfectam/0.6

Figure 2:
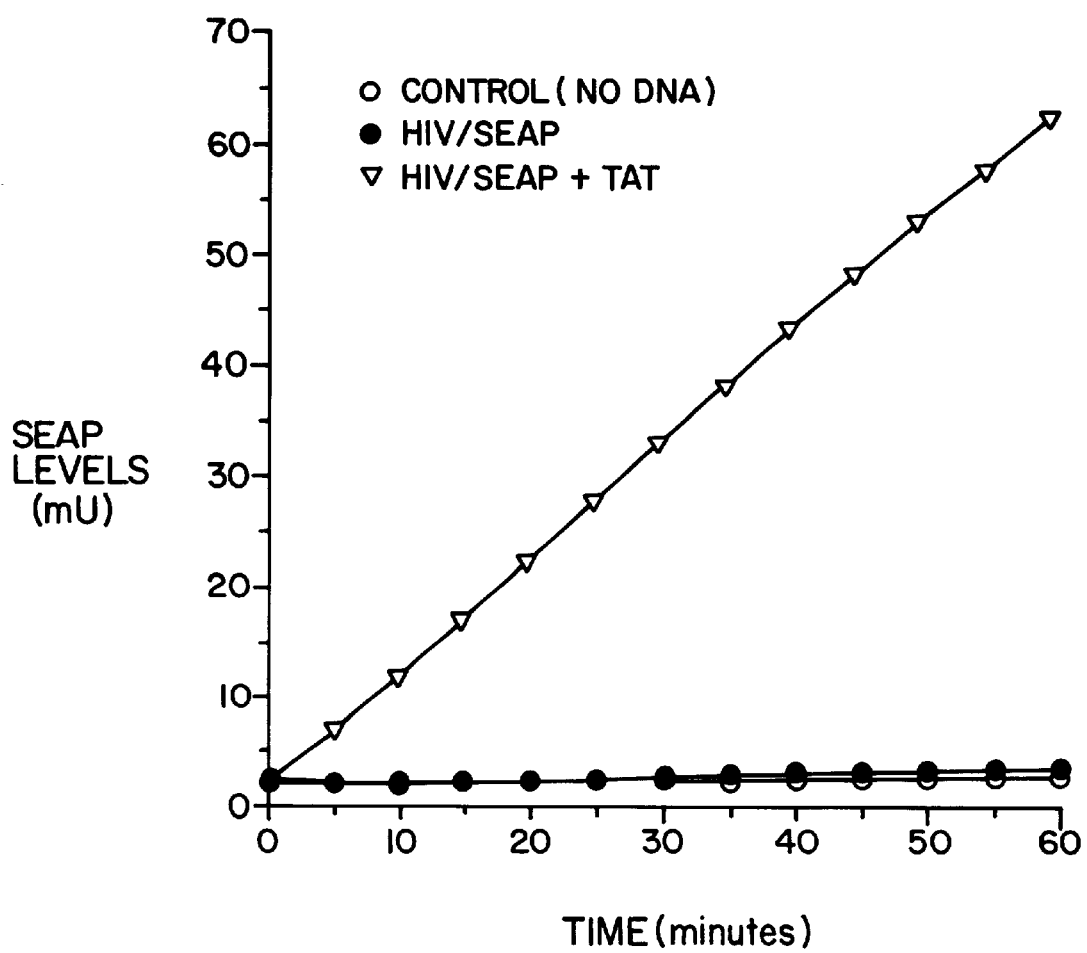
FIG. 2 demonstrates the induction of the secreted alkaline phosphatase (SEAP) expression in the standard SEAP assay.

The results of Tat-induced SEAP levels in the standard assay after optimization of these conditions, are illustrated in FIG. 2. Briefly, COS cells were maintained in Isocove's Modified Dulbecco's Medium (IMDM) supplemented with 10% fetal calf serum (FCS) and antibiotics. Triplicate cell samples were seeded at a density of ≈1.5×10$^5$ cells per well in Linbro® 24 flat bottom wells of 17-mm diameter and incubated in a humidified 95% $O_2$/5% $CO_2$ incubator at 37° C. until they reached 50% confluency. Subconfluent cells were transfected using the lipospermine procedure (Loeffler and Behr, *Methods in Enzymology* 217: 599–618, 1993). The medium of the subconfluent cells was aspirated and replaced by 300 µl of fresh minimum medium (IMDM supplemented with 3% FCS). COS cells were transfected with either pBC12/HIV/SEAP alone (0.35 µg/well) or pBC12/CMV/t2 (coding for Tat function) at 0.175 µg/well+pBC12/HIV/SEAP (0.35 µg/well) or with buffer alone (no DNA control samples). The plates were incubated for 12 to 15 hours after which, 700 µl of complete medium (IMDM containing 10% FCS) were added. Cells were then incubated for 48 hours after which, a 250-µl aliquot was removed from COS cell culture supernatants and heated at 65° C. for 5 minutes to selectively inactivate endogenous phosphatases (SEAP is heat stable). The samples were then centrifuged in a microfuge for 2 minutes. One hundred µl of 2×SEAP assay buffer (1.0 M diethanolamine, pH 9.8; 0.5 mM $MgCl_2$; 10 mM L-homoarginine) were added to 100-µl aliquot of the samples. The solution was mixed and transferred into a 96-well flat-bottom culture dish (Corning). Twenty µl of pre-warmed substrate solution (120 mm p-nitrophenylphosphate dissolved in 1×SEAP assay buffer) were dispensed with a multipipetter into each well containing the reaction mixture. $A_{405}$ of the reaction was read at 5-minute intervals at 37° C. for 60 minutes using an EL340i microplate reader (Bio-tek Instruments, Inc.) with 5-seconds automatic shaking before each reading. The change in absorbance was converted in mU of SEAP expression as previously described (Berger et al., *Gene* 66: 1–10, 1988) and plotted against time.

These results indicate a nearly 65-fold increase in SEAP induction after 1 hour relative to the control (no DNA) levels or the induction of nonselected gene (HIV/SEAP) alone.

Assay-Guided Isolation of Creosote Bush Extract Active Component(s) by Countercurrent Chromatography: As stated above, the differential fractionation and purification by countercurrent chromatography (CCC) of the creosote bush extract constituents led to the isolation of two major components (Table 1). 6.8 mg of the component termed Gr was isolated from the Green fraction on $Sio_2$ TLC. The total percent yield was ≈0.051% based on the original plant powder. 9.3 mg of the component Lo was isolated from the Yellow fraction (Ye).

Figure 3:
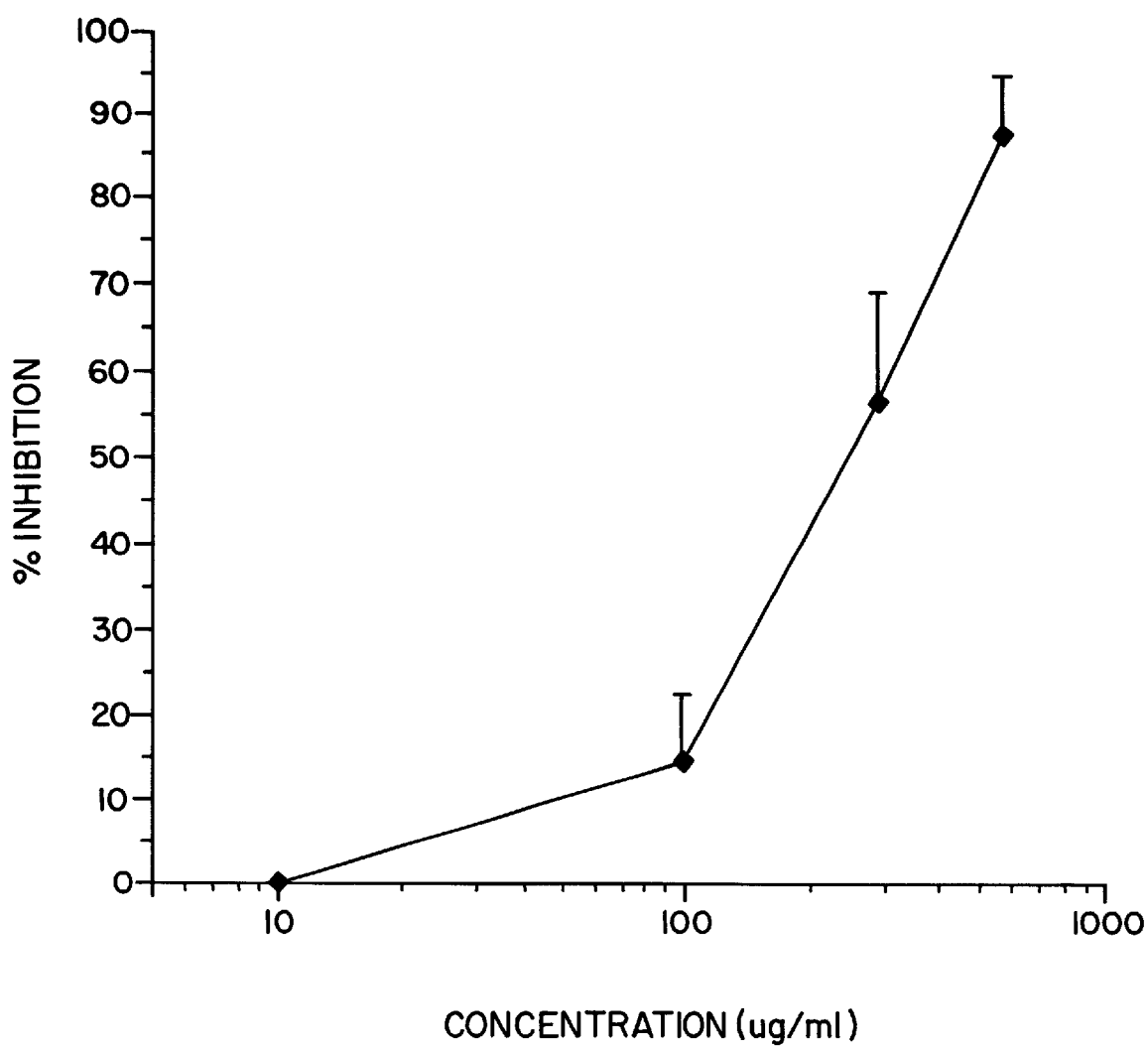
FIG. 3 shows the inhibition of Tat-TRS activity by creosote bush total extract in the secreted alkaline phosphatase (SEAP) assay.

Inhibition of Tat-TRS Activity by Extracts from Creosote Bush Leaves and Flowers: In several plant extracts tested with the SEAP assay, only the extract from the creosote bush, *Larrea tridentata*, leaves and flowers showed significant inhibitory activity of HIV Tat protein. Creosote bush displayed a dose-response inhibition of SEAP expression as illustrated in FIG. 3. Briefly, triplicate samples of COS cells were transfected with a mixture of pBC12/HIV/SEAP and pBC12/CMV/t2 (coding for Tat function) in 2:1 ratio, using the lipospermine procedure as described above. Cells were incubated for 12–15 hours after transfection. Creosote bush extract stock solution (10 mg/ml) was made in calcium/magnesium-free PBS and 10% DMSO, and filter-sterilized using a Millex®-GS 22 µm filter (Millipore). The appropriate concentrations of creosote bush extract were added to the transfected cells at a final DMSO concentration of 0.2% and samples were incubated for 48 hours. For SEAP analysis, a 250-µl aliquot was removed from COS cell culture supernatants, heated at 65° C. for 5 minutes to selectively inactivate endogenous phosphatases (SEAP is heat stable) and centrifuged in a microfuge for 2 minutes. One hundred µl of 2×SEAP assay buffer (1.0 M diethanolamine, pH 9.8; 0.5 mM $MgCl_2$; 10 mM L-homoarginine) were added to 100-µl aliquot of the samples. The solution was mixed and transferred into a 96-well flat-bottom culture dish (Corning). Twenty µl of pre-warmed substrate solution (120 mM p-nitrophenylphosphate dissolved in 1×SEAP assay buffer) were dispensed with a multipipetter into each well containing the reaction mixture. $A_{405}$ of the reaction was read at 5-minute intervals at 37° C. for 60 minutes using an EL340i microplate reader (Bio-tek Instruments, Inc.) with 5-second automatic shaking before each reading. The percent inhibition of SEAP expression was calculated at 30 minutes as follows:

% Inhibition=100−[($CT^+$−$C^+$)/($CT^-$−$C^-$)×100]

where:

| | |
|---|---|
| $C^-$ | Control sample (no DNA, no drug) |
| $CT^-$ | Control sample (+ DNA, no drug) |
| $C^+$ | Drug-treated sample (no DNA, + drug) |
| $CT^+$ | Drug-treated sample (+ DNA, + drug) |

As seen in FIG. 3, the onset of this inhibition started at a concentration of 20 µg/ml and reached a maximum inhibitory activity at 600 µg/ml. The estimated $EC_{50}$ (the concentration exhibiting 50% of inhibition) for this crude material was 110 µg/ml. As the purification of the active ingredients progressed, there was a stepwise increase in the activity of the active ingredient(s) which tripled (68%) with the organic phase (OG) fraction compared to 21% from the original total crude extract.

Inhibition of HIV Cytopathic Effects: A compound inhibiting Tat transactivation should in principle block HIV replication. Consequently, creosote bush extract was tested at the National Cancer Institute (NCI) for inhibition of HIV-1 cytopathic effects using the soluble-formazan assay (Weislow et al., *JNCI* 81: 577–586, 1989, the entire contents of which are hereby incorporated by reference and relied upon). In principle, CEM-SS cells (ATCC, Rockville, Md.) are cocultivated with HIV-producing H9 cells. Viruses infect the host CEM-SS cells, replicate and kill most of the CEM-SS cells in a week. If the drug inhibits HIV production, CEM-SS cells are protected from HIV-induced cell death. The tetrazolium (XTT) reagent is therefore metabolically reduced by the viable cellsc to yield a colored formazan product which is measurable by colorimetry at 450 nm.

In practice, triplicate samples of CEM-SS cells (5000) were plated in 96-well microtiter plate. Appropriate concentrations of test compounds were added in a final volume of 100 μl calcium/magnesium-free PBS in 5% DMSO. Control samples received the compound medium (PBS) alone. Five minutes later, 500 highly infectious HIV-1 producing H9 cells or normal H9 cells were added to the wells containing the appropriate drug concentrations. The microtiter plates were incubated at 37° C. in 95% $O_2$/5% $CO_2$ for 6 days after which a 50-μl mixture of XTT and N-methylphenazonium methosulfate (PMS) was added. The plates were reincubated for additional 4 hours for the color development (XTT formazan production). The plates were sealed, their contents were mixed by automatic shaking and the $OD_{450}$ of samples was determined in a microplate reader. Each value represents the average of 3 determinations. No significant difference was found between the means of the duplicate values of the uninfected cells and HIV-challenged cells, in presence of test compounds. In contrast, there was a significant difference (p<0.05) between HIV-challenged samples in the presence or absence of test compounds.

The results of these studies are summarized in Table 2. At a concentration of 0.75 μg/ml for component Gr, there was an average 58% protection (cell viability) against HIV as opposed to 15% viability in drug-free samples challenged with HIV. At a concentration as low as 0.187 μg/ml, component Lo exhibited even stronger inhibitory activity of HIV cytopathic effects. The cell viability was 87%, very close to that of not treated control cells (89%), in contrast to 14% viability for the drug-free samples challenged with HIV. These compounds were devoid of cytotoxicity at the concentrations used.

Figure 4:
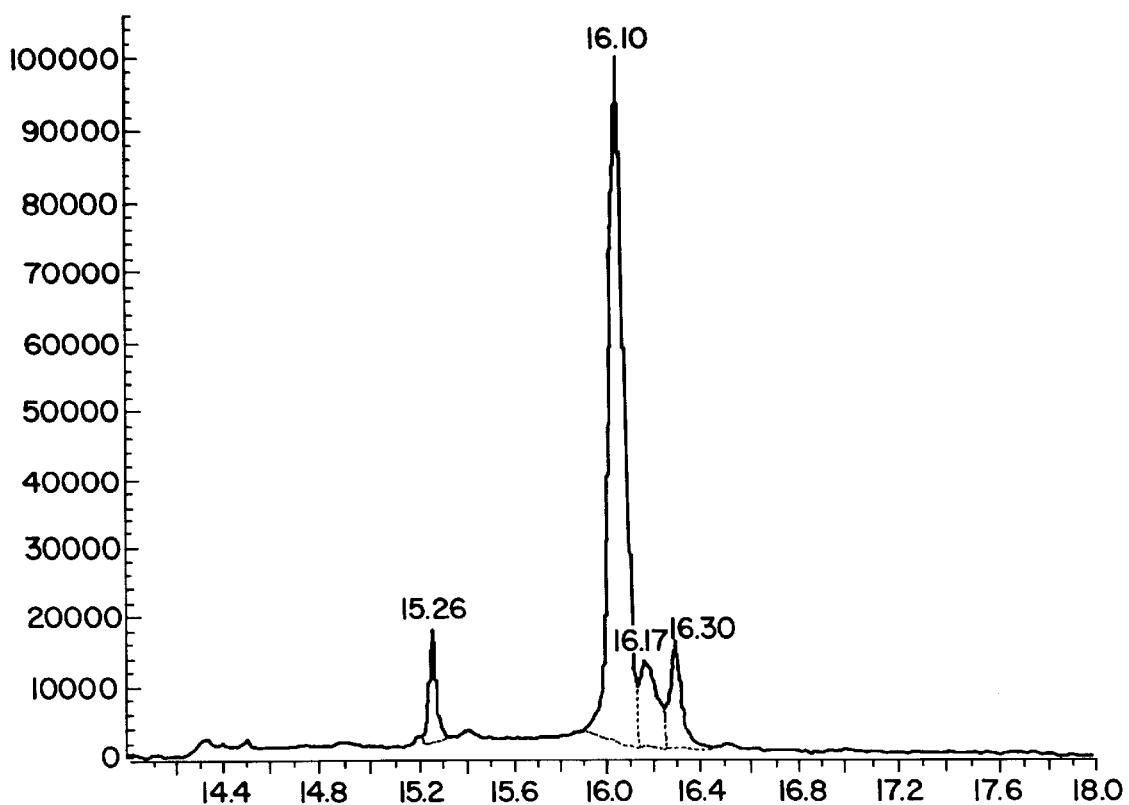
FIG. 4 shows an analysis of plant-derived HIV Tat inhibitors in Component Lo by gas chromatography (GC) using an analytical non-destructive capillary cross-linked 5% phenyl-methylsiloxane (HP-5) column. Component Lo is a mixture of four components. The time (minutes) of elution appears on each peak.

Structure elucidation of the active components of creosote bush extract: The chemical characterization of the purified plant active constituents was achieved mainly by mass spectroscopy and by H- and C-nuclear magnetic resonance (NMR). Component Lo was found to be a mixture of four related compounds (L1, L2, L3 and L4). Resolution and characterization of each peak of the mixture was accomplished by gas chromatography (GC) using an analytical non-destructive capillary cross-linked 5% phenylmethylsiloxane (HP-5) column attached to a mass spectroscope (MS). The GC studies revealed that the first compound (L1) represented 6% of the mixture; the second (L2) was 76% of the mixture (MW=316); the third (L3) was isomeric with L2 and represented 9% of the total mixture (MW=316); and the fourth compound (L4) represented 9% of the mixture (MW= 358). The time (minutes) of elution of these compounds is indicated on the peaks (FIG. 4).

Figure 5:
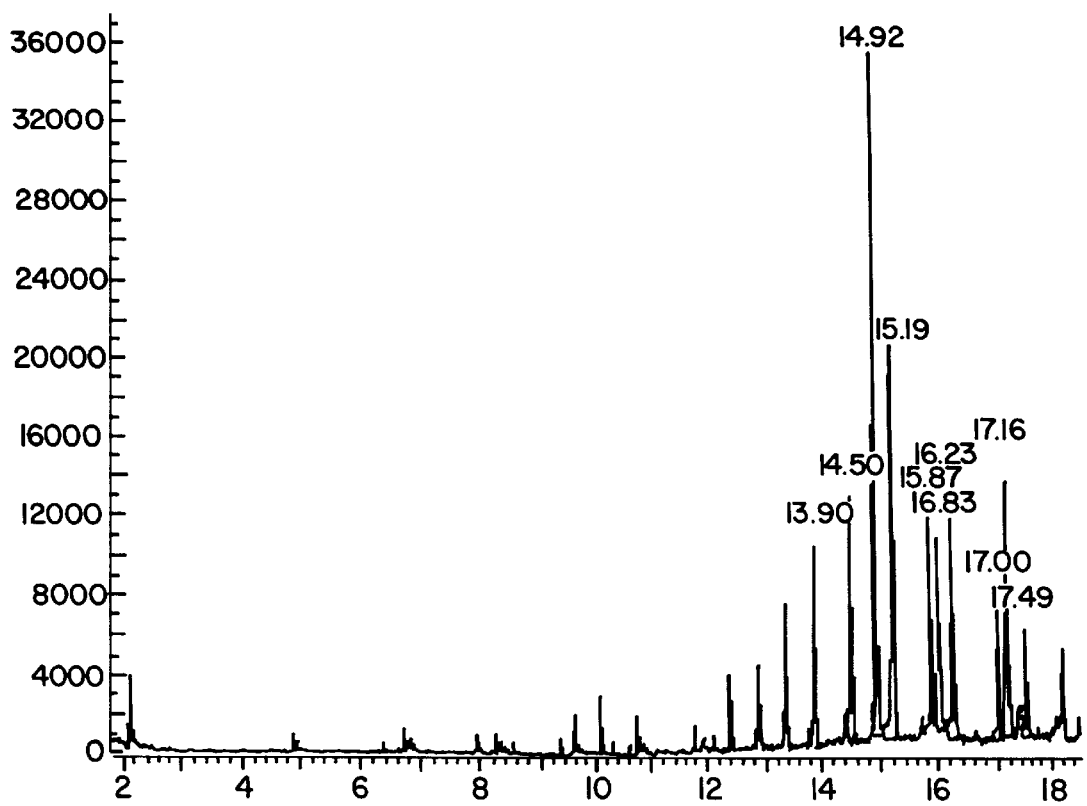
FIG. 5 shows an analysis of plant-derived HIV Tat inhibitors in Component Gr by gas chromatography (GC) using an analytical non-destructive capillary cross-linked 5% phenylmethylsiloxane (HP-5) column. Component Gr is a complex mixture. The time (minutes) of elution appears on each peak.

Component Gr consisted of fifteen compounds. Resolution and characterization of each peak of the mixture was accomplished by gas chromatography (GC) using analytical non-destructive capillary cross-linked 5% phenylmethylsiloxane (HP-5) column attached to a mass spectroscope (MS). The GC studies revealed that four (G1, G2, G3 and G4) of the fifteen compounds are lignans and structurally related to the L compounds. The time (minutes) of elution of these compounds is indicated on the peaks (FIG. 5).

The structures of these eight compounds (L1, L2, L3, L4, G1, G2, G3 and G4) are described as follows:

L1 has the composition $C_{18}H_{22}O_4$ and has been identified as a previously known chemical, 1,4-bis-(3,4-dihydroxyphenyl)-2,3-dimethylbutane (nordihydroquaiaretic acid, NDGA, Merck Index, 10th Edition, #6534). The structural formula for L1 is as follows:

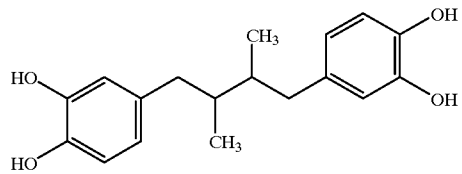

L2 has the composition $C_{19}H_{24}O_4$ and has been identified as 3-O-methyl-NDGA or 1-(3,4-dihydroxyphenyl)-4-(3-methoxy-4-hydroxyphenyl)-2,3-dimethylbutane. The structural formula for 3-O-methyl-NDGA is as follows:

TABLE 2

INHIBITION OF HIV-1 CYTOPATHIC EFFECTS BY CREOSOTE
BUSH EXTRACT COMPOUNDS IN THE SOLUBLE-FORMAZAN ASSAY.

| Test Sample | Concentration of the test sample which yielded max protection against HIV without killing the cells μg/ml | Percent of live cells at day 6 as measured by XXT Formazan production | | |
|---|---|---|---|---|
| | | Uninfected plus test sample | HIV infected plus test sample | HIV infected minus test sample |
| Fraction Green | 0.187 | 59 | 67 | 16 |
| Component $G_r$ - duplicates | 0.75 | 80 | 67 | 16 |
| Component $G_r$ | 0.75 | 70 | 48 | 14 |
| Fraction Yellow (Ye) | 0.187 | 60 | 57 | 14 |
| Component $L_o$ - duplicates | 0.187 | 91 | 86 | 14 |
| Component $L_o$ | 0.187 | 89 | 87 | 14 |

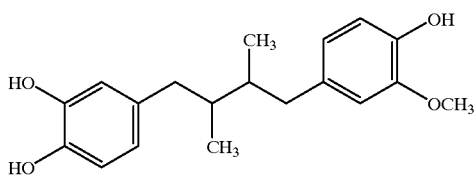

L3 also has the composition $C_{19}H_{24}O_4$ and has been identified as 4-O-methyl-NDGA or 1-(3,4-dihydroxyphenyl)-4-(3-hydroxy-4-methoxyphenyl)-2,3-dimethylbutane. 4-O-methyl-NDGA is also known as *Malachi* 4:5–6 or Mal 4. The structural formula for 4-O-methyl-NDGA is as follows:

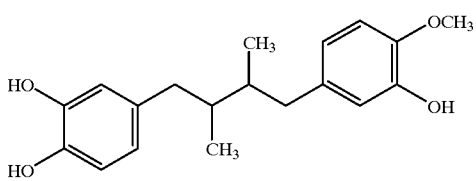

L4 has the composition $C_{21}H_{26}O_5$ and has been identified as 3-O-methyl-4-O-acetyl-NDGA or 1-(3,4-dihydroxyphenyl)-4-(3-methoxy-4-acetoxyphenyl)-2,3-dimethylbutane. The structural formula for 3-O-methyl-4-O-acetyl-NDGA is as follows:

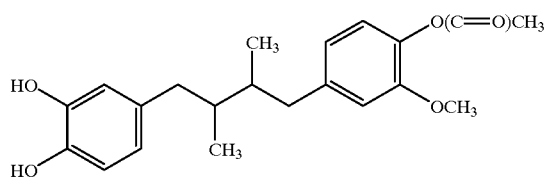

G1 has a molecular weight of 344, a composition of $C_{21}H_{22}O_4$ and has been identified as 3,3',4-tri-O-methyl-NDGA or 1-(3-hydroxy-4-methoxyphenyl)-4-(3,4-dimethoxyphenyl)-2,3-dimethylbutane. 3,3',4-tri-O-methyl-NDGA has the following structural formula:

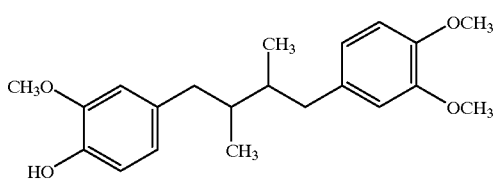

G2 has a molecular weight of 344, a composition of $C_{21}H_{22}O_4$ and has been identified as 3,4,4'-tri-O-methyl-NDGA or 1-(3-methoxy-4-hydroxyphenyl)-4-(3,4-dimethoxyphenyl)-2,3-dimethylbutane. The structural formula for 3,4,4'-tri-O-methyl-NDGA is as follows:

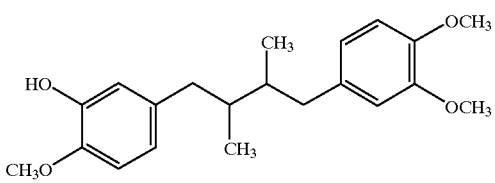

G3 and G4 each has a molecular weight of 372 and a composition of $C_{22}H_{28}O_5$. G3 is either 3',4-di-O-methyl-3-O-acetyl-NDGA (as in G3a) or 3,3'-di-O-methyl-4-O-acetyl-NDGA (as in G3b).

3',4-di-O-methyl-3-O-acetyl-NDGA is also known as 1-(3-methoxy-4-hydroxyphenyl)-4-(3-acetoxy-4-methoxyphenyl)-2,3-dimethylbutane and has the following structural formula:

G3a:

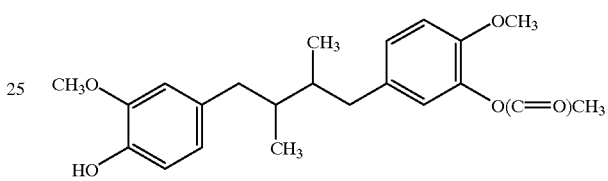

3,3'-di-O-methyl-4-O-acetyl-NDGA is also known as 1-(3-methoxy-4-hydroxyphenyl)-4-(3-methoxy-4-acetoxyphenyl)-2,3-dimethylbutane and has the following structural formula:

G3b:

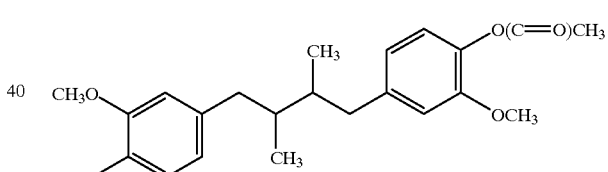

Similarly, G4 is either 4,4'-di-O-methyl-3-O-acetyl-NDGA (as in G4a) or 3,4'-di-O-methyl-4-O-acetyl-NDGA (as in G4b). 4,4'-di-O-3-O-acetyl-NDGA is also known as 1-(3-hydroxy-4-methoxyphenyl)-4-(3-acetoxy-4-methoxyphenyl)-2,3-dimethylbutane and has the following structural formula:

G4a:

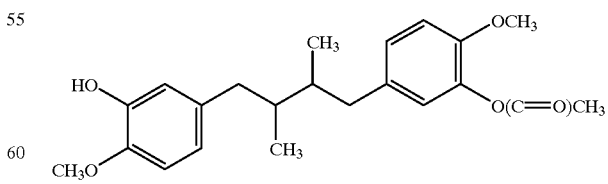

3,4'-di-O-methyl-4-O-acetyl-NDGA is also known as 1-(3-hydroxy-4-methoxyphenyl)-4-(3-methoxy-4-acetoxyphenyl)-2,3-dimethylbutane and has the following structural formula:

G4b:

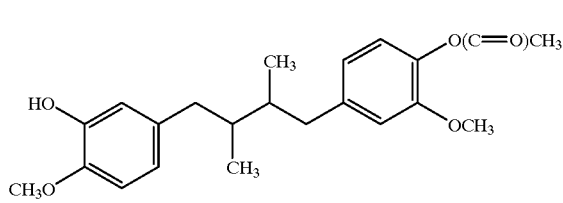

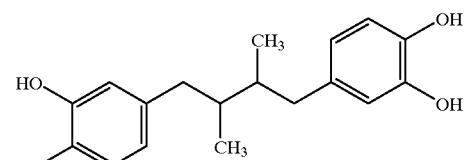

In addition to the above described isolation and purification procedures, each disclosed derivative of NDGA may be prepared by chemical synthesis following either methylation and/or acetylation of NDGA according to the procedure of Ikeya et al., Chem. Pharm. Bull. 27(7): 1583–1588, 1979, the entire contents of which are hereby incorporated by reference and relied upon.

Large scale purification of component Lo and two pure compounds (L2 and L3) from component Lo: A large scale CCC fractionation of a batch of plant materials was initiated to generate a larger quantity of component Lo. A total of 110 g plant powder was first treated with 700 ml hexane 5 times. The hexane soluble materials (1.17 g) were discarded. The hexane insoluble material (HI fraction) was dried and extracted 3 times by successive macerations with 800 ml chloroform:methanol. This afforded 20 g of total extract (Tex) which was combined with 7.6 g of HI fraction obtained from a previous batch differential extraction. A 27.6 g total. of crude plant materials thus generated was divided into two batches of 10 g and 17.6 g. These batches were initially run separately on the large-capacity versatile Cross-Axis CPC (Shinomiya et al., J. Chromatogr. 644:215–229, 1993, the entire contents of which are hereby incorporated by reference) using the solvent system hexane:EtOAc:MeOH:0.5% NaCl in 6:4:5:5 ratio with the upper phase (organic layer) as the mobile phase. The fractions were pooled exclusively according to the TLC patterns and four major fractions were identified from the two CCC operations and denoted fraction Green (Gr)(1.12 g), fraction Lo (2.87 g), fraction End (1.78 g) and finally, the stationary phase SP (20.84). The entire 2.87 g of fraction Lo was further fractionated in the large model triplet CPC with the hexane:EtOAc:MeOH:H$_2$O system in 7:3:5:5 ratio, using the aqueous layer as mobile phase. Four fractions denoted LYI (0.375); LYII (0.113 g); LYIII (0.280 g) and LYIV (2.80 g) were identified according to the elution order and the TLC patterns. These fractions were assayed for anti Tat-TRS activity at 10 μg/ml. Based on the test results, LYI was selected for further purification.

Isolation of L2 and L3 pure compounds from LYI fraction of component Lo: The less hydrophobic fraction LYI was selected for further purification using the previously improved conditions, i.e., the triplet CPC and Hex:CHCl$_3$:MeOH:10 mM NaCl solvent system in 1:4:4:2 ratio. This afforded preparation of 148 mg of homogeneous L3 and 109.3 mg of pure L2 as examined by NMR and mass spectroscopy. The structures of L3 (Malachi4:5–6) and L2 have been described above.

Figure 6:
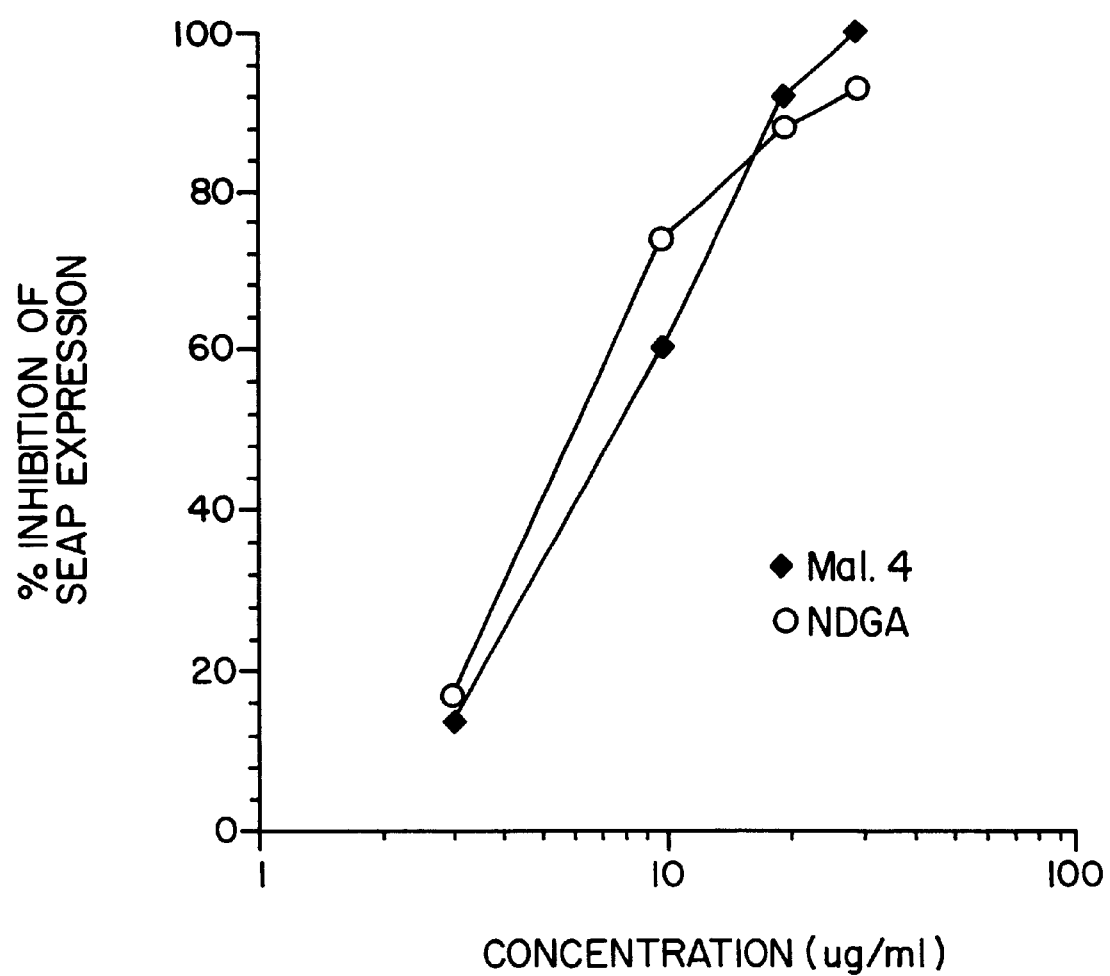
FIG. 6 illustrates the inhibition of Tat-induced SEAP expression by the plant-derived single compound Malachi 4:5–6 (Mal 4) and NDGA in the secreted alkaline phosphatase (SEAP) assay.

Compounds L2 and L3 are derivatives of a previously identified chemical, 1,4-bis-(3,4-dihydroxyphenyl)-2,3-dimethyl butane (nordihydroquaiaretic acid, NDGA, Merck Index, 10th Edition, #6534). The structural formula for NDGA, which is identical to that of Li described above, is as follows:

The anti-HIV activity (the inhibition of Tat regulated HIV transactivation) of NDGA and its derivatives was previously unknown. Comparative anti-HIV transactivation activity for NDGA and derivative Malachi4:5–6 (Mal 4) are illustrated in FIG. 6. Briefly, duplicate samples of subconfluent COS cells were co-transfected with plasmid pBC12/HIV/SEAP and pBC12/CMB/t2 (coding for Tat function) using the lipospermine procedure as described above. Cells were then incubated for 12–15 hours. The test compounds were initially solubilized in 10% DMSO/calcium-magnesium-free PBS and added to the transfected cells in the appropriate concentrations at a final DMSO concentration of 0.2%. The samples were incubated for 48 hours after which, a 250-μl aliquot was removed from COS cell culture supernatants, and SEAP was analyzed as in the standard assay as in FIG. 3. The percent inhibition of SEAP expression was calculated at 30 minutes as follows:

% Inhibition=100−[(CT$^+$−C$^+$)/(CT$^-$−C$^-$)×100]

where:

| | |
|---|---|
| C$^-$ | Control sample (no DNA, no drug) |
| CT$^-$ | Control sample (+ DNA, no drug) |
| C$^+$ | Drug-treated sample (no DNA, + drug) |
| CT$^+$ | Drug-treated sample (+ DNA, + drug) |

Each point represents the average of two determinations. No significant difference was apparent between the EC$_{50s}$ of Mal 4 and NDGA which were 8 μg/ml (25 μM) and 6 μg/ml (20 μM), respectively. The EC$_{50s}$ are defined as the inhibitory concentration of the compound at which the Tat regulated HIV transactivation is reduced to 50% of that in untreated control cells.

The inhibition of transactivation of HIV promoter activity by Mal 4 and NDGA were compared in Table 3.

TABLE 3

INHIBITION OF TRANSACTIVATION OF HIV PROMOTER ACTIVITY BY NATURAL COMPOUNDS MAL 4 and NDGA.

| Test Compound | Inhibition of Tat-induced Seap Expression (% inhibition/concentration of test compound) | | | | | | | |
|---|---|---|---|---|---|---|---|---|
| | % | μm | % | μm | % | μm | % | μm |
| Mal 4 | 13.6 | 9.5 | 60.4 | 31.3 | 92 | 62.7 | 100 | 95 |
| NDGA | 17.0 | 9.9 | 73.8 | 32.6 | 88.1 | 65.2 | 92.9 | 99 |

The compounds NDGA and Mal 4 were assayed as described for FIG. 6. Control samples were run in quadruplicate. The percentage inhibition was determined after 30 minutes and the OD$_{405}$ values were:

| | |
|---|---|
| C⁻ | Control sample (no DNA, no drug): 0.091 |
| CT⁻ | Control sample (+DNA, no drug): 0.805. |

Figure 7:
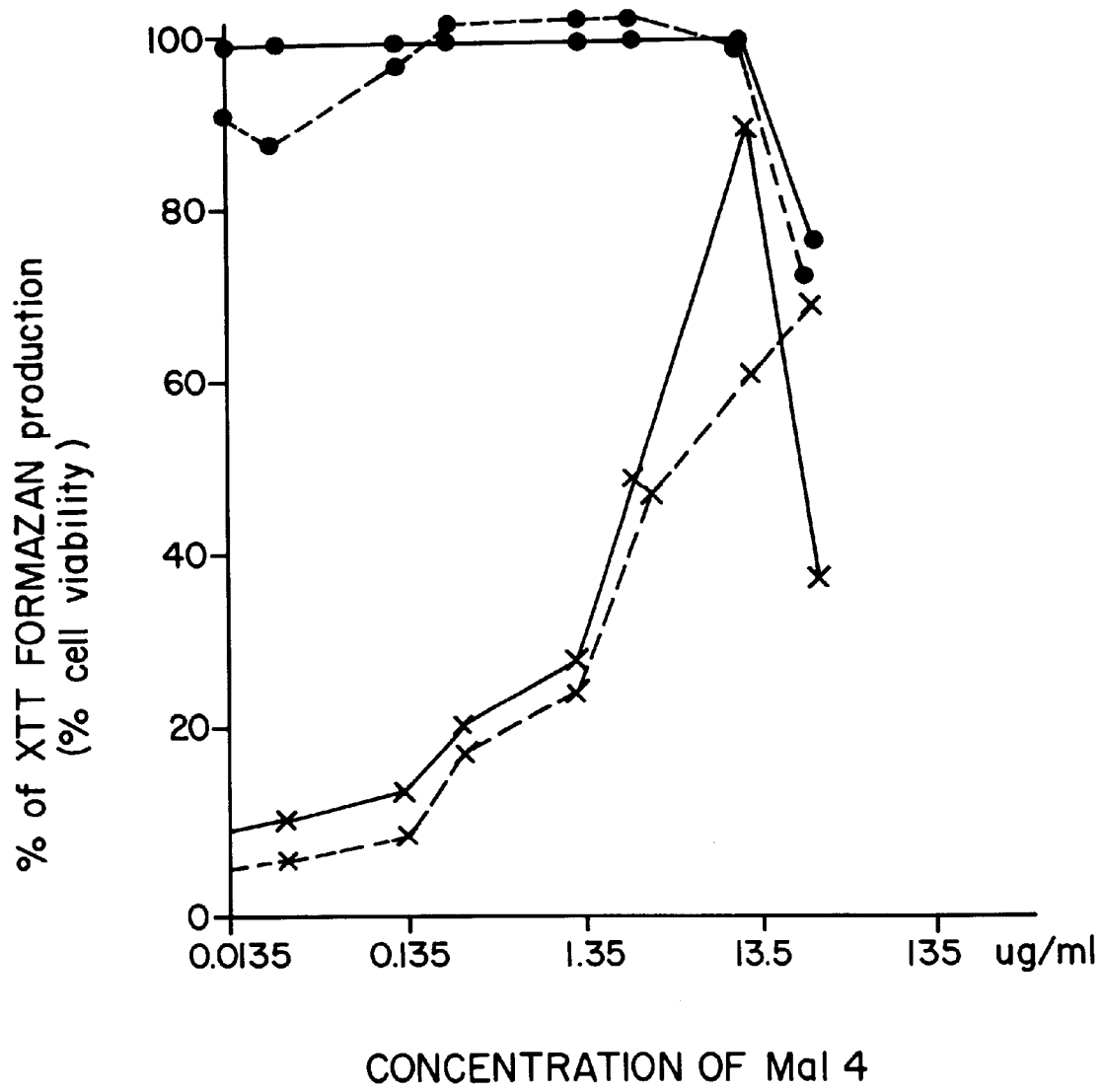
FIG. 7 depicts the quantitation of XTT formazan production as a measurement of viable cells in Mal 4 treated cultures of either HIV infected or uninfected CEM-SS cells in two separate experiments. The percent XTT formazan production for infected cells without Mal 4 treatment for experiment 1 was 8.9% and for experiment 2 was 7.5%. For experiment 1, uninfected cells are represented by •-• and infected cells by x-x. In experiment 2, uninfected cells are represented by •- - -• and infected cells by x - - - x. The $EC_{50}$ was found to be 4.25 μg/ml or 13.4 μM. The $IC_{50}$ was estimated to be 100 μg/ml or 325 μM.

The quantitation of XTT formazan production as a measurement of viable cells in Mal 4 treated cultures of CEM-SS cells in shown in FIG. 7. Each figure shows infected or uninfected CEM-SS target cells ($10^4$/M well) with serial dilutions of Mal 4. $EC_{50}$. represents the concentration of Mal 4 (e.g. 13.4 µM) that increases (protects) XTT formazan production in infected culture to 50% of that in uninfected, untreated culture cells. $IC_{50}$ represents inhibitory or toxic concentration of Mal 4 (e.g., 325 µM, estimated) that reduces XTT formazan production in uninfected cultures to 50% of that in untreated, uninfected control cells. Levels of XTT formazan in untreated, infected control cells were 9% of those in untreated, uninfected control cells. The soluble-formazan assay for HIV-1 cytopathic effects was conducted according to the procedure described by Weislow et al., *JNCI* 81: 577–586, 1989, the entire contents of which are hereby incorporated by reference and relied upon.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

Thus, it is to be understood that variations in the derivatives of NDGA and the method of suppression of Tat transactivation can be made without departing from the novel aspects of this invention as defined in the claims.

What is claimed is:

1. A compound having the following structural formula:

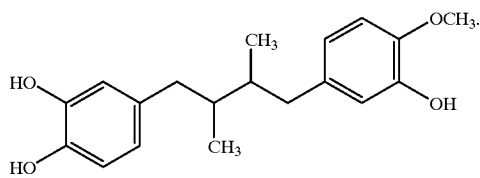

2. A compound having the following structural formula:

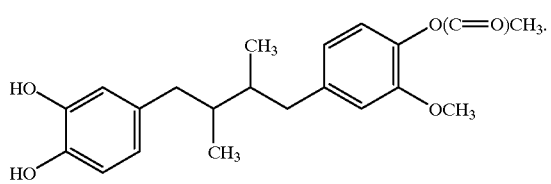

3. A compound having the following structural formula:

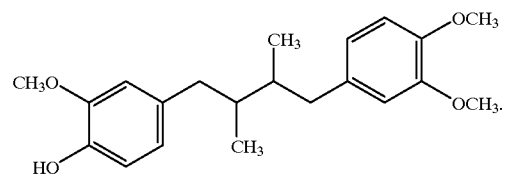

4. A compound having the following structural formula:

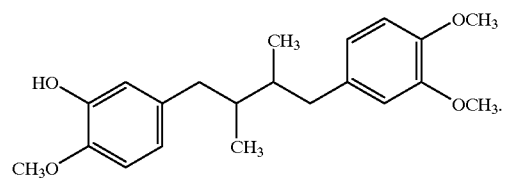

5. A compound having the following structural formula:

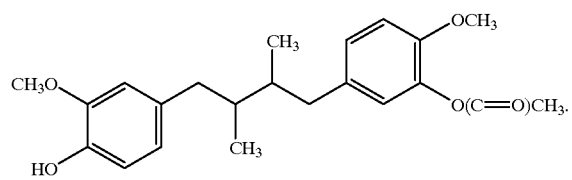

6. A compound having the following structural formula:

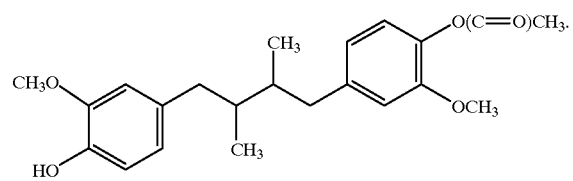

7. A compound having the following structural formula:

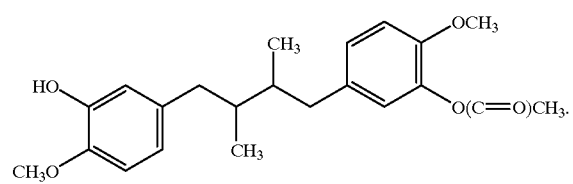

8. A compound having the following structural formula:

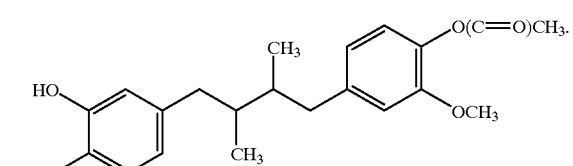

* * * * *